United States Patent
Neumann

(10) Patent No.: US 8,405,833 B2
(45) Date of Patent: Mar. 26, 2013

(54) METHOD TO DETERMINE THE SATIN-EFFECT ON METAL PLATED SUBSTRATES

(75) Inventor: Stefan Neumann, Berlin (DE)

(73) Assignee: Atotech Deutschland GmbH, Berlin (DE)

( * ) Notice: Subject to any disclaimer, the term of this patent is extended or adjusted under 35 U.S.C. 154(b) by 0 days.

(21) Appl. No.: 13/265,576

(22) PCT Filed: May 25, 2010

(86) PCT No.: PCT/EP2010/057135
§ 371 (c)(1),
(2), (4) Date: Oct. 21, 2011

(87) PCT Pub. No.: WO2010/136439
PCT Pub. Date: Dec. 2, 2010

(65) Prior Publication Data
US 2012/0081710 A1    Apr. 5, 2012

(30) Foreign Application Priority Data
May 25, 2009    (EP) .................................... 09161012

(51) Int. Cl.
*G01N 21/47*    (2006.01)
(52) U.S. Cl. ........................ 356/446; 356/448
(58) Field of Classification Search .................. 356/445, 356/446, 448, 300, 326, 237.1–237.6, 601; 250/271; 382/108
See application file for complete search history.

(56) References Cited

U.S. PATENT DOCUMENTS

| | | | |
|---|---|---|---|
| 5,218,417 A | 6/1993 | Gay et al. | |
| 7,460,218 B2 | 12/2008 | Schwarz | |
| 2003/0159940 A1 | 8/2003 | Schulz et al. | |
| 2008/0231865 A1 | 9/2008 | Schwarz et al. | |

FOREIGN PATENT DOCUMENTS

GB    2277148    10/1994

OTHER PUBLICATIONS

PCT/EP2010/057135; PCT International Search Report and Written Opinion of the International Searching Authority mailed Sep. 16, 2010.
"OptoSurf : Oberflachennnessung in der Fertigung" [Online] Jan. 1, 2008, OPTOSURF, Company Brochure, Germany, pp. 1, XP002549617. Retrieved from the Internet on Oct. 9, 2009: URL:http://www.optosurf.com/pdf/optosurf-Datenblatt.pdf.

*Primary Examiner* — Tri T Ton
(74) *Attorney, Agent, or Firm* — Renner, Otto, Boisselle & Sklar, LLP

(57) ABSTRACT

Subject of the present application is a method to determine the satin-effect on metal plated substrates comprising the following steps: i) irradiate the sample with light, ii) detect the intensity distribution of the scattered light, iii) determine at least one of the following parameters:—the Aq value of the intensity distribution, wherein the Aq value represents the variance of the backscattered light angle ($\phi_i$) multiplied with the device constant k and—the integrated intensity of the intensity distribution, iv) compare the at least one parameter to a target value.

9 Claims, 7 Drawing Sheets

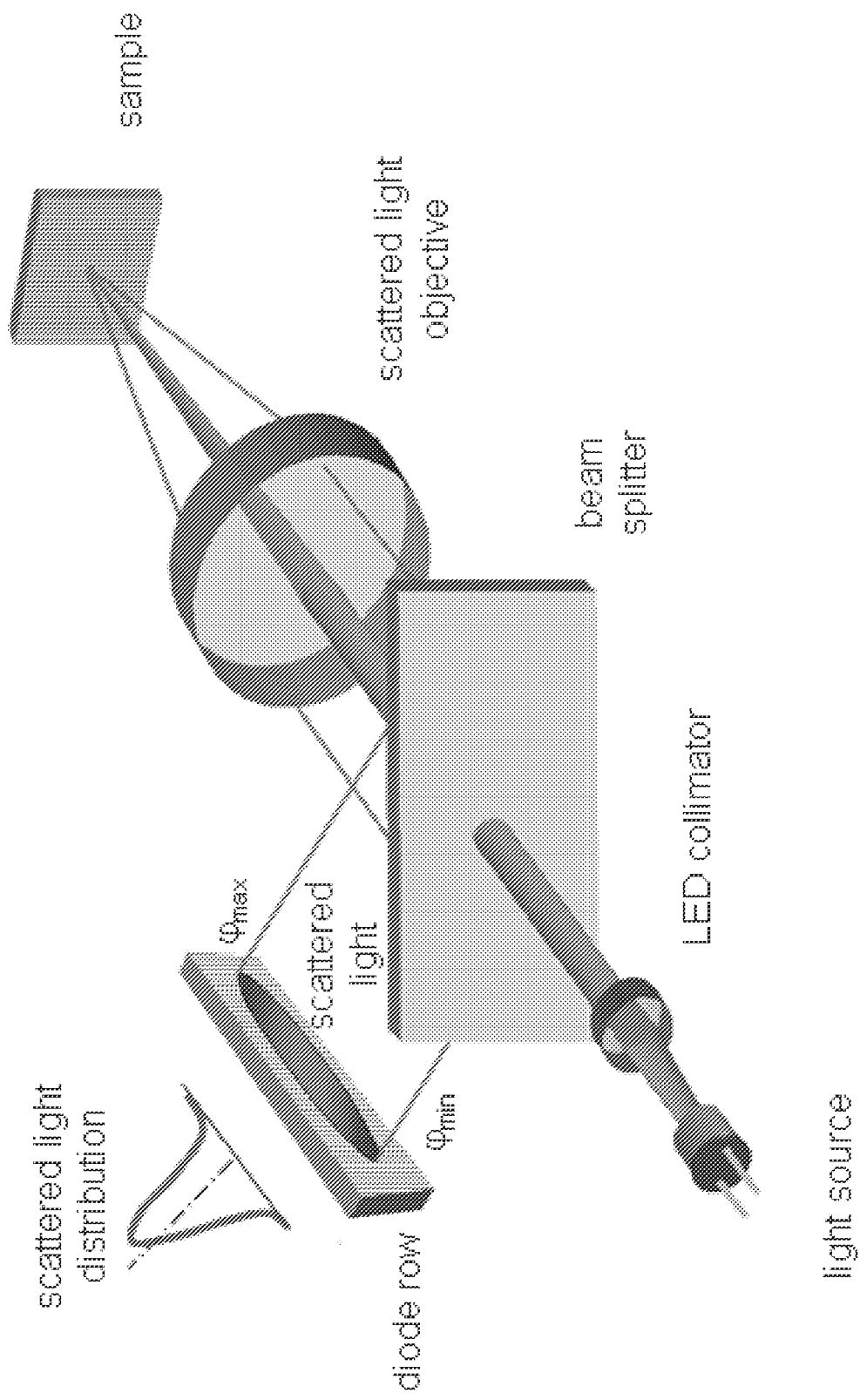
Fig. 1 Assembly to detect the intensity distribution of the scattered light (principle)

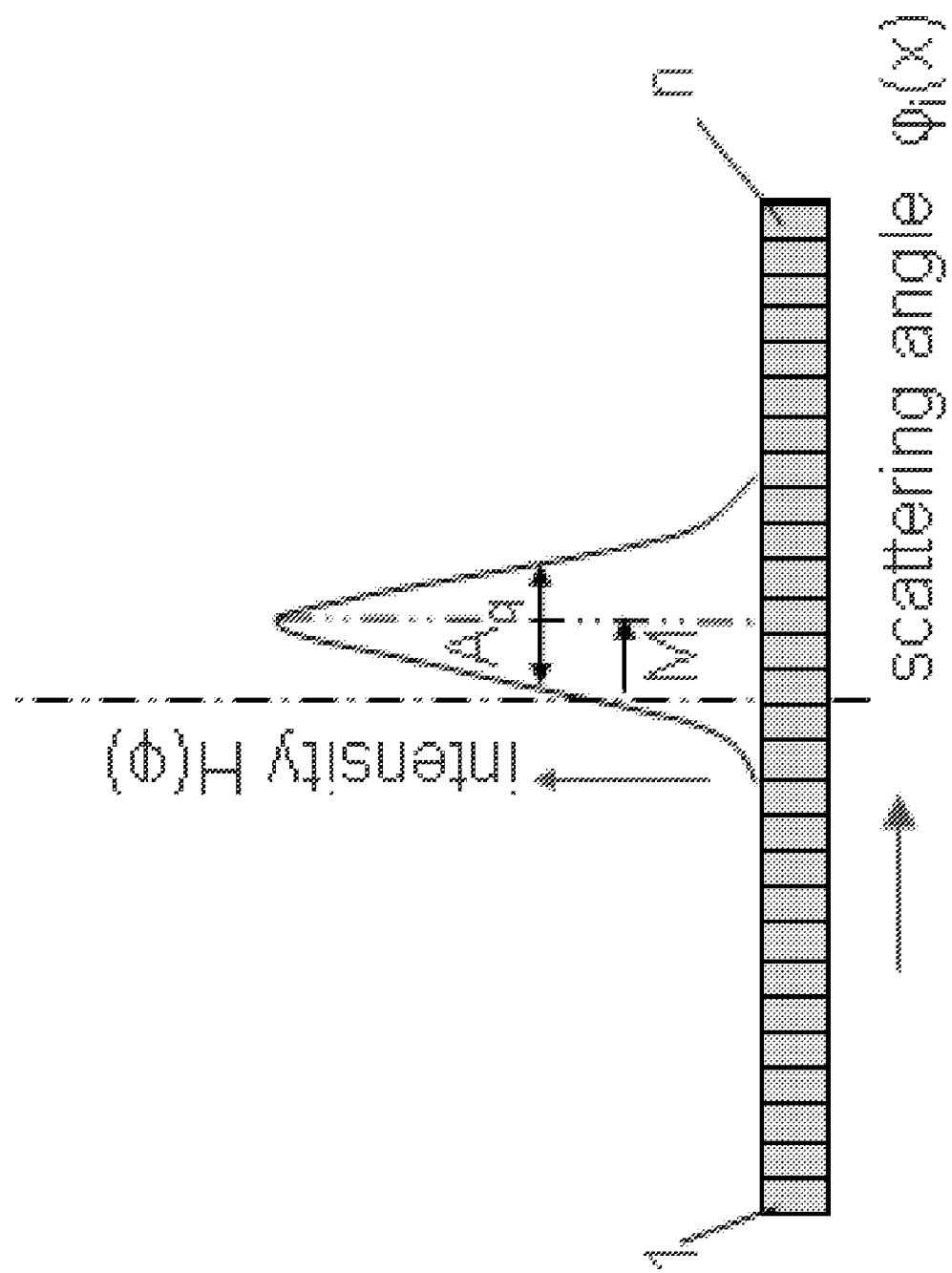
Fig. 2 Intensity distribution of the scattered light.

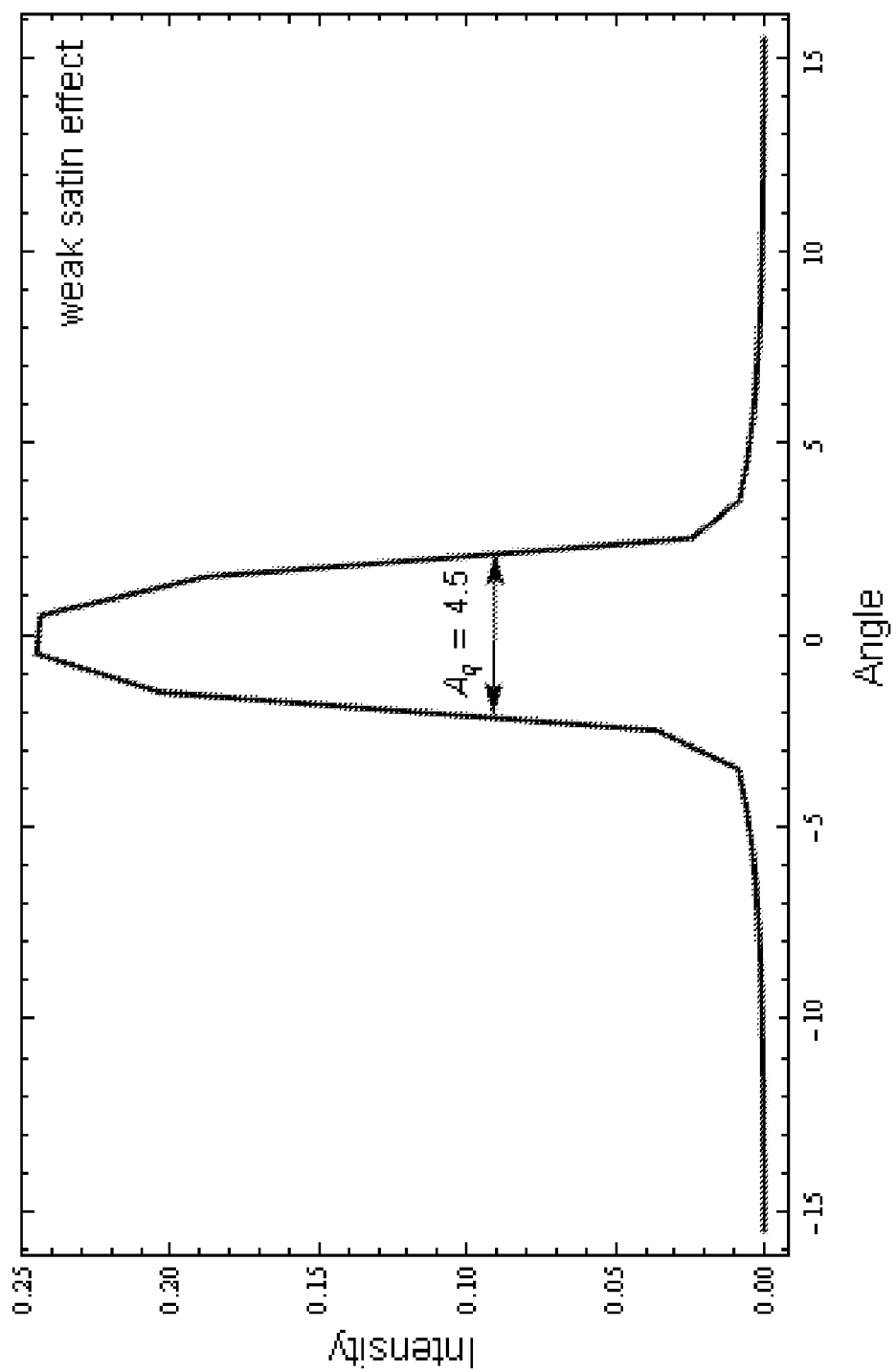
Fig. 3 Intensity distribution of the backscattered light for a weak satin-effect.

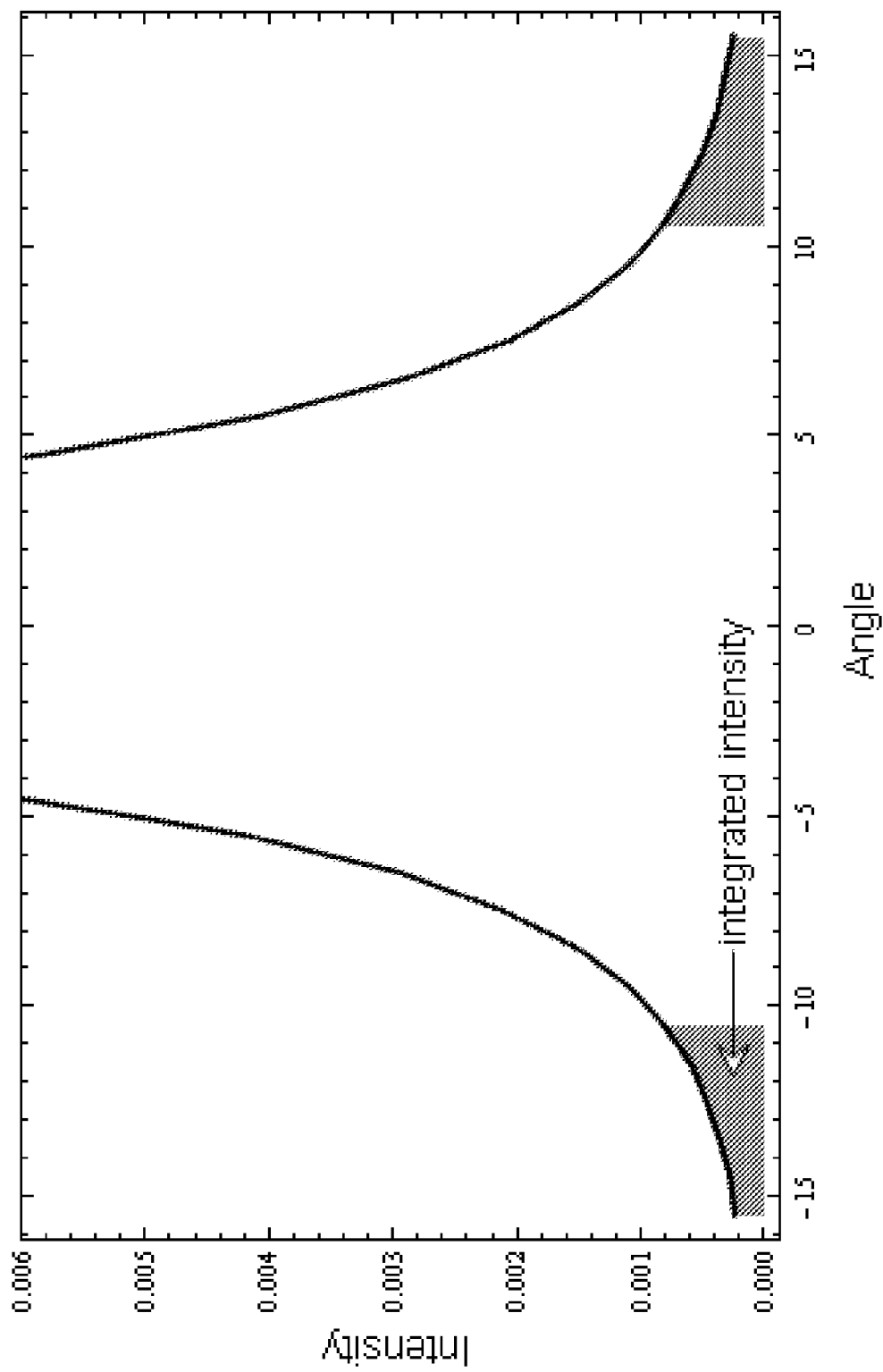
Fig. 4 Zoomed out part from Fig. 3. Illustration of integrated intensity at high angles.

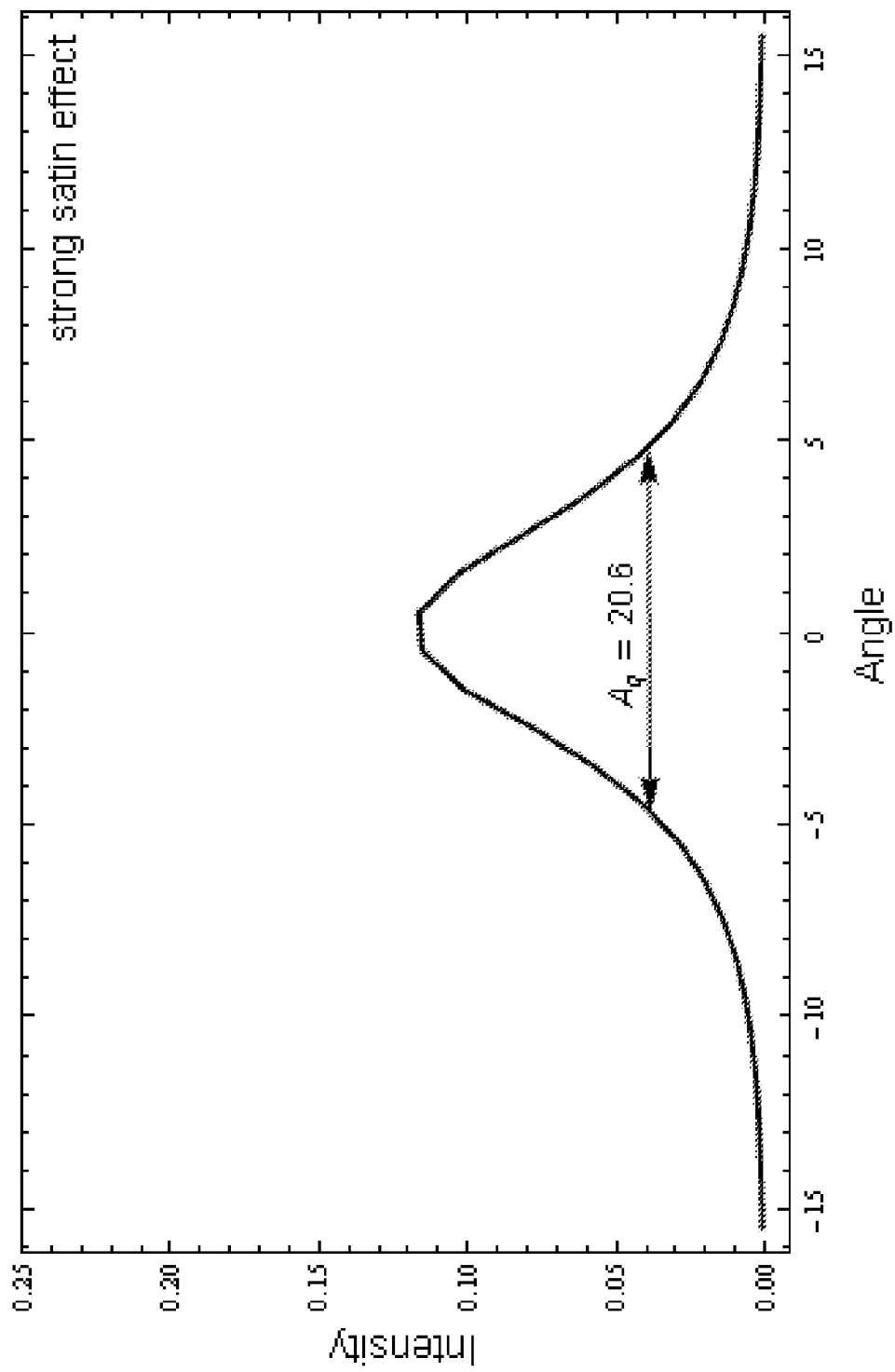
Fig. 5 Intensity distribution of the backscattered light for a strong satin-effect.

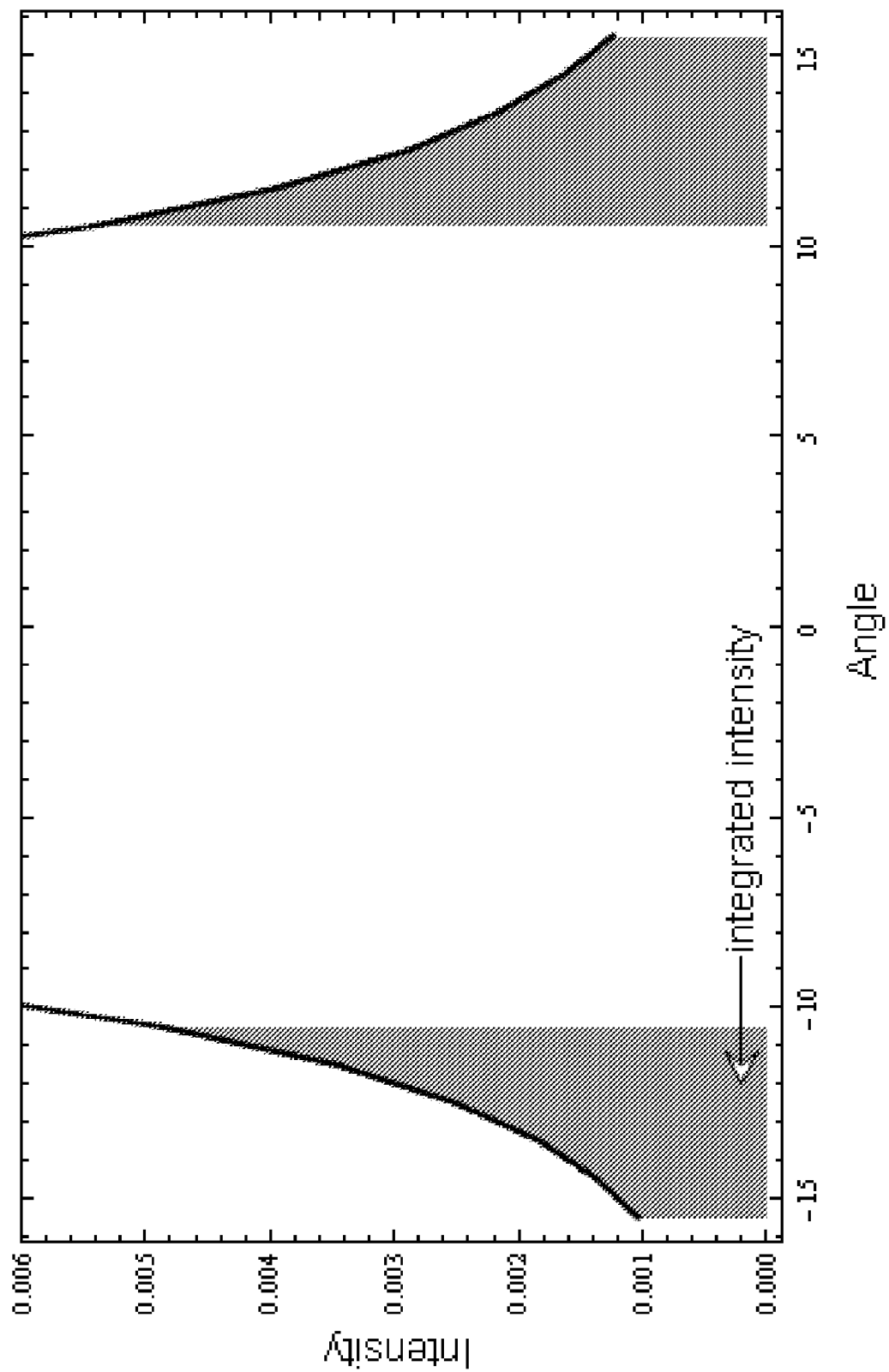
Fig. 6 Zoomed out part from Fig. 5. Illustration of integrated intensity at high angles.

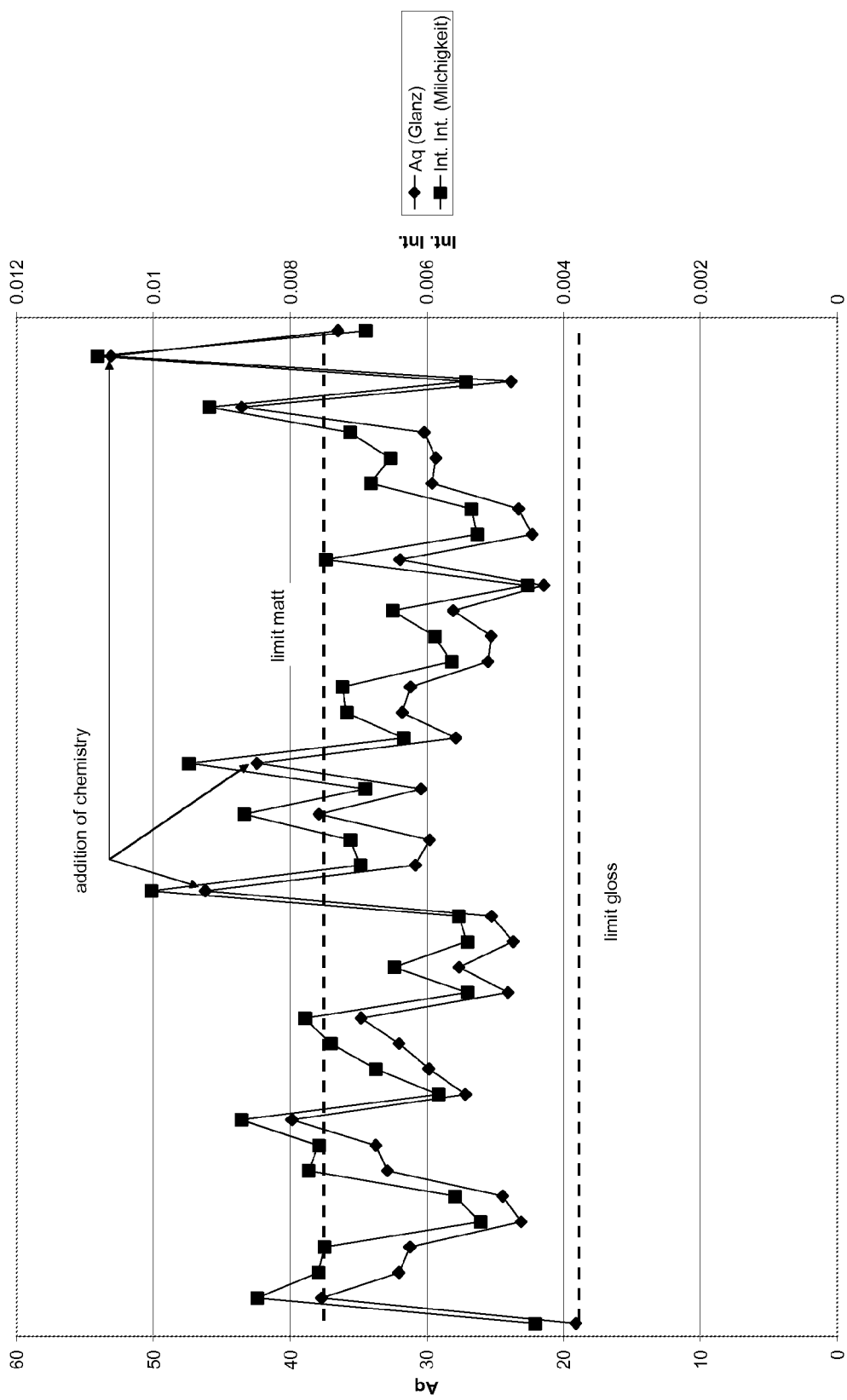
Fig. 7 Plating results during the production cycle with regards to the values of Aq and integrated intensity.

METHOD TO DETERMINE THE SATIN-EFFECT ON METAL PLATED SUBSTRATES

FIELD OF THE DISCLOSURE

The invention relates to a method to evaluate the satin-effect (alternative terms used comprise gloss level or "Satilume" effect) of metal surfaces, e.g. of chromium or nickel surfaces by means of scattered light measurement.

In contrast to the present way of determining the satin-effect by visual inspection the results of the scattered light method are not influenced by the human factor and are therefore very reliable and highly reproducible.

BACKGROUND OF THE INVENTION

The satin-effect of surfaces is achieved by a co-deposition of small particles or droplets during the electroplating process of the respective metal, e.g. nickel. The additives used for this process are adsorbed to the substrate surface causing small pits of about 0.1-0.2 μm depth and 2-20 μm in diameter. This causes a diffused light reflection on the, e.g. nickel surface. Depending on the plating process parameters, type of additives and their concentrations, many different degrees of satin-effects can be achieved. Examples for metal plating baths to produce a satin-effect are for example described in EP 1 287 184.

In order to achieve an even satin-finished nickel or nickel alloy coating an acid nickel or nickel alloy electroplating bath is proposed which contains a sulfosuccinic acid compound of the general formula (I) additional to at least one quaternary ammonium compound, wherein R1, R2=hydrogen ion, alkali ion, alkaline earth ion, ammonium ion and/or C1-C18 hydrocarbon moiety.

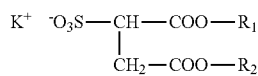

Formula I

At present the satin-effect of metal plated surfaces is determined by optical inspections of skilled employees by visually comparing pre-plated standard samples with plated samples from the plating line. This leads to results with a low reproducibility which are strongly influenced by the human factor.

A demand exists for a method to reliably measure the satin-effect (gloss level) of metal plated surfaces which resulted in the development of a method using scattered light according to the present invention.

BRIEF DESCRIPTION OF THE DRAWINGS

FIG. 1 shows a schematic drawing of a setup to measure the intensity distribution of scattered light.

FIG. 2 shows a schematic drawing of an intensity distribution of scattered light. A segmented diode row 1 is shown.

FIG. 3 shows the measured intensity distribution of a surface with a weak satin-effect.

FIG. 4 shows a zoomed out part of FIG. 3 illustrating the integrated intensity.

FIG. 5 shows the measured intensity distribution of a surface with a strong satin-effect.

FIG. 6 shows a zoomed out part of FIG. 5 illustrating the integrated intensity.

FIG. 7 shows plating results during the production cycle with regards to the values of Aq and integrated intensity.

DETAILED DESCRIPTION OF THE INVENTION

The method to describe the satin-effect by analysing the back scattered light needs a light source (e.g. LED) to illuminate the investigated surface.

The light is focussed and directed perpendicular onto the surface to be analysed. The back scattered light is collected and its angular intensity distribution is detected by measuring the intensity at several discrete positions/angles (see FIG. 1).

As a light source preferably a light-emitting diode (LED) is being used. LEDs of a wavelength range between 350-800 nm can be used. For example a LED emitting red light in the range of 610-760 nm can be used.

Referring to FIGS. 1 and 2 as an intensity detector a diode row is provided consisting of a number of discrete diodes, e.g. n=28 (FIG. 2). The width of the diode row determines the maximum angle distribution of the scattered light which can be detected, i.e. W=φ(max)−φ(min). The light from the light source is directed to the sample, preferably using a beam splitter and optionally a lense (FIG. 1 "scattered light objective") to focus the light before it contacts the sample. The light is scattered on the surface and directed to the diode row 1 (FIG. 2) for detection of its intensity distribution for different angles. Preferably a beam splitter is used to direct the scattered light to the LED diode row for measurement.

The intensity distribution contains the information needed to describe the gloss level and the haze of the sample surface. While the gloss level specifies the mirror properties of the sample surface the haze describes an underlying "milky" effect. Both the gloss and haze together specify the satin effect.

The gloss level can be specified by the parameter Aq (shown in FIG. 2) which describes the width of the normalized intensity distribution of the scattered light.

FIG. 2 shows the diode row having a number of n diodes to detect the intensity of the scattered light H (φ) for a certain scattering angle φi (x).

To calculate the Aq value the following equations are used $$M = \Sigma \phi_i * H(\phi_i)$$  Equation (1)

and $$Aq = k * \Sigma (\phi_i - M)^2 * H(\phi i)$$  Equation (2)

The parameter M gives the angular distance of the maximum peak of the intensity distribution to the angle of reflection 0° or in other words M is the expected value for the angle of the backscattered light φ with distribution function $H(\phi_i)$ (FIG. 2). M should be zero as in this case the incoming light is perpendicular to the sample surface. Therefore, sample surface and detector should be aligned that M is (nearly) zero. M is obtained by the sum of the product of the scattering angle $\phi_i$ and the scattering intensity $H(\phi_i)$ (Equation (1)). The Aq value is obtained by Equation (2) (factor k being a device constant), variance of the back-scattered light angle ($\phi_i$) multiplied with the device constant k. As can be seen by the Equation 1 the Aq value represents the central moment of order two (means variance) of the backscattered light angle φ.

A low Aq value is achieved when most of the incoming light is scattered at low angles (direct reflection, FIG. 3). That means a low Aq value represents high direct reflection (high gloss and only a small satin-effect). On the other hand a high Aq value is measured when the light is scattered over a wide area of the angle of reflection (low gloss, strong satin-effect, FIG. 5).

Generally, one can assume that an Aq value of 10, preferably 20 or higher indicates a satin-effect. A typical range of Aq values suitable for production varies from an Aq value between 20 and 40 as indicated in FIG. 7. Usually a very strong satin-effect is obtained by an Aq value of 50-60. A mirror-like surface with essentially total reflection possesses an Aq value of only 1-4.

The amount of light which is scattered at high angles (e.g. between 10° to 15° and −10° to −15°) causes an effect called haze. Typically, the integration at high angles comprises an integration between angles of preferably 10° to 15° and −10° to −15°, alternatively between 5° to 15° and −5° to −15°, alternatively between 10° to 25° and −10° to −25° or even 10° to 35° and −10° to −35°. Generally the higher the angle value, the lower the contribution to the integrated intensity is. By integrating the intensity distribution of the scattered light at high angle intervals one obtains the degree of haze the sample surface shows. The higher the integrated intensity the higher the haze effect (see FIGS. 4 and 6). FIG. 4 shows the integrated value of the intensity for a sample possessing a low satin-effect. As can be seen from the graph the integrated area is small compared to the overall area of the backscattered light. In contrast, FIG. 6 shows the integrated value of the intensity for a sample possessing a strong satin-effect. As can be seen from the graph the integrated area is higher compared to the overall area of the backscattered light than in FIG. 4. The value of the integrated intensity unlike the Aq value is no reliable indicator of the satin-effect. Only in special cases the measurement of the integrated intensity alone serves to determine the satin-effect of metal surfaces. In most cases, the integrated intensity only in combination with the Aq value is a good means to determine the satin-effect of a said surface. Generally, a first sample has a lower haze than a second sample when the integrated intensity of the first sample is lower than the integrated intensity of the second sample and when the Aq values of the samples are of the same or almost the same value.

FIG. 7 exhibits values for the integrated intensity, which range from about 0.004 to 0.008 (right ordinate). The values are the average integrated intensity of the −10° to −15° and 10° to 15° intervals. A value of 0.004 indicate that 0.8% of the area of the intensity of the scattered light is within said angle interval.

Example 1

Test samples having a satin nickel surface were prepared using a commercially available satin-effect plating process (SATILUME® PLUS AF, Atotech Deutschland GmbH). The substrates plated and analysed according to the present invention were 7 cm×20 cm sized copper sheets which were electroplated for 20 minutes at a plating bath temperature of 55° C. and a cathodic current density of 2.5 A/dm² using above mentioned satin-effect nickel plating bath.

The test samples were measured using the following instrument to measure the intensity distribution of the scattered light: OS 500 from company OptoSurf (k=1.17 for Equation 2).

For each sample the Aq value and the value of the integrated intensity was determined which corresponds to acceptable visual limits of the satin-effect on the nickel plated samples. The limits are shown in FIG. 7 (limit matte and limit gloss) and correspond to well defined values of Aq and the integrated intensity. Thereafter, both the Aq and the integrated intensities were measured during the production of plated samples. As can be seen from FIG. 7 the values of Aq and the integrated intensity provide a good tool for quality control of the plated samples. Addition of plating bath additives which provide the satin-effect during production can result in unsatisfactory plating results with regards to the satin-effect as shown in FIG. 7 (measuring points denoted "addition of chemistry"). By using the measurement method according to the present invention the best amount of additives to be added can be determined.

The invention claimed is:

1. Method to determine with a device constant k the satin-effect on metal plated substrates comprising the following steps:
   i) irradiate a sample with light from a light source,
   ii) detect the angular intensity distribution $H(\phi_i)$ of the backscattered light,
   iii) determine both of the following parameters:
      the Aq value of the angular intensity distribution $H(\phi_i)$, wherein the Aq value represents the variance of the backscattered light angle $\phi_i$ multiplied with the device constant k $Aq = k * \Sigma (\phi_i - M)^2 * H(\phi_i)$ wherein $M = \Sigma \phi_i * H(\phi_i)$ and the integrated intensity of the angular intensity distribution, and
   iv) compare both of the parameters to a target value.

2. Method according to claim 1 wherein the wavelength of the light ranges between 350 nm and 800 nm.

3. Method according to claim 1 wherein the wavelength of the light ranges between 610 nm and 760 nm.

4. Method according to claim 1 wherein the source of light is a LED.

5. Method according to claim 1 wherein the target value is determined from a sample having a predefined satin-effect represented by the Aq value, the integrated intensity or both.

6. Method according to claim 1 wherein the integrated intensity value is determined by integrating an interval of 10° to 15° and −10° to −15°.

7. Method according to claim 1 wherein the Aq target value ranges between 10 and 60.

8. Method according to claim 1 wherein the Aq target value ranges between 20 and 40.

9. Method according to claim 1 wherein the plated metal layer having a satin-effect is nickel.

* * * * *